United States Patent [19]

Lucas et al.

[11] Patent Number: 5,879,666
[45] Date of Patent: *Mar. 9, 1999

[54] METHODS AND COMPOSITIONS FOR REDUCING BODY ODOR

[75] Inventors: Juliet Marie Lucas, Cincinnati; Robert Gregory Bartolo, Montgomery, both of Ohio; Michael Thomas Dodd, Florence, Ky.; Toan Trinh, Maineville, Ohio; Robin Yager Buckner, Cincinnati, Ohio; Theresa Marie Kajs, Loveland, Ohio

[73] Assignee: The Procter & Gamble Company, Cincinnati, Ohio

[ * ] Notice: The term of this patent shall not extend beyond the expiration date of Pat. Nos. 5,871,718 and 5,871,719.

[21] Appl. No.: 947,075

[22] Filed: Oct. 8, 1997

Related U.S. Application Data

[63] Continuation-in-part of Ser. No. 736,471, Oct. 24, 1996, abandoned.

[51] Int. Cl.$^6$ .............................. A61K 7/32; A61K 25/00; A61K 33/10; A61K 33/24
[52] U.S. Cl. .................................. 424/65; 422/5; 424/67; 424/69; 424/76.1; 424/76.2; 424/76.21; 424/76.4; 424/76.8; 424/78.03; 424/405; 424/642; 424/715; 424/717
[58] Field of Search ................................ 424/65, 67, 69, 424/76.1, 76.2, 76.21, 76.4, 76.8, 78.03, 405, 642, 715, 717; 422/5

[56] References Cited

U.S. PATENT DOCUMENTS

| | | | |
|---|---|---|---|
| 3,172,817 | 3/1965 | Leupold et al. | 167/90 |
| 3,426,011 | 2/1969 | Parmerter et al. . | |
| 3,453,257 | 7/1969 | Parmerter et al. . | |
| 3,453,258 | 7/1969 | Parmerter et al. . | |
| 3,453,259 | 7/1969 | Parmerter et al. . | |

(List continued on next page.)

FOREIGN PATENT DOCUMENTS

| | | |
|---|---|---|
| 0 613 675 A1 | 9/1994 | European Pat. Off. . |
| 0701812 A1 | 3/1996 | European Pat. Off. . |
| 2201880 | 5/1974 | France . |
| 87637 | 11/1972 | Germany . |
| 2731520 | 1/1979 | Germany . |
| 229304 A1 | 11/1985 | Germany . |
| 208482 B | 8/1992 | Hungary . |
| 53-41440 | 4/1978 | Japan . |
| 58-124452 | 7/1983 | Japan . |
| 61-128973 | 6/1986 | Japan . |
| 63-164953 | 7/1988 | Japan . |
| 3-170415 | 7/1991 | Japan . |
| 3-284616 | 12/1991 | Japan . |
| 05-269185 | 10/1993 | Japan . |
| 1472536 | 5/1977 | United Kingdom . |
| WO 91/12029 | 8/1991 | WIPO . |
| WO 94/22500 | 10/1994 | WIPO . |
| WO 95/17175 | 6/1995 | WIPO . |
| WO 96/04937 | 2/1996 | WIPO . |
| WO 96/04938 | 2/1996 | WIPO . |
| WO 96/04940 | 2/1996 | WIPO . |
| WO 96/05358 | 2/1996 | WIPO . |

OTHER PUBLICATIONS

Leyden, "Bacteriology of the Human Axilla: Relationship to Axillary Odor", Antiperspirants & Deodorants, 1988, pp. 311–319.

Lachman, et al., The Theory and Practice of Industrial Pharmacy, 1986, pp. 466–467; 520–522; 458–461.

Loftsson, T., et al., "Interactions Between Preservatives and 2–Hydroxypropyl–β–Cyclodextrin", Drug Development and Industrial Pharmacy, 18(13) (1992),pp. 1477–1484.

Furuta, T., et al., "Effects of Water and Alcohol on the Formation of Inclusion Complexes of d–limonene and Cyclodextrins", Supramolecular Chemistry, vol. 1 (1993), pp. 321–325.

Furuta, T., et al., "Formation of Inclusion Complex Between Cyclodextrin and d–limonene by a Twin Screw Kneader", The 7th International Cyclodextrins Symposium, Tokyo, Japan (Apr. 25–28, 1994), pp. 512–515.

Hashimoto, H., "Studies on the Industrial Production and Application of Cyclodextrins", Starch Science, vol. 36, No. 1 (1989), pp. 35–42.

Hashimoti, H., "Application of Cyclodextrins to Foods, Toiletries and Other Products in Japan", Ensuiko Sugar Refining Co., Ltd., pp. 13–46.

Lehner, S. J., et al., "Interactions Between p–hydroxybenzoic Acid Esters and Hydroxypropyl–β–Cyclodextrin and Their Antimicrobial Effect Against *Candida Albicans*", International Journal of Pharmaceuticals, 93 (1993), pp. 201–208.

Djedaini–Pilard, F., et al., "Optimal Performances with Minimal Chemical Modifications of Cyclodextrins", The 7th International Cyclodextrins Symposium, Tokyo, Japan (Apr. 25–28, 1994) pp. 94–97.

Lehner, S. J., et al., "Effect of Hydroxypropyl–β–Cyclodextrin on the Antimicrobial Action of Preservatives", J. Pharm. Pharmacol, vol. 46 (1994), pp. 186–191.

*Primary Examiner*—Shelley A. Dodson
*Attorney, Agent, or Firm*—Kirsten K. Stone; Mary Catherine Hentz; Douglas C. Mohl

[57] ABSTRACT

The present invention relates to an odor absorbing composition, which is safe for use on human skin comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, and skin protectants; an emulsifier; and an aqueous carrier. The odor absorbing compositions of the present invention may also contain an effective amount of hydrophobic antimicrobials.

The present invention also relates to methods of using the compositions of the present invention to reduce body odor and/or vaginal odor. The composition can be applied directly as a spray, poured from a bottle and applied by hand, or applied via a wipe.

23 Claims, No Drawings

U.S. PATENT DOCUMENTS

| | | | |
|---|---|---|---|
| 3,453,260 | 7/1969 | Parmerter et al. . | |
| 3,459,731 | 8/1969 | Gramera et al. . | |
| 3,553,191 | 1/1971 | Parmerter et al. . | |
| 3,565,887 | 2/1971 | Parmerter et al. . | |
| 3,574,821 | 4/1971 | Pfirrmmann et al. | 424/45 |
| 4,078,051 | 3/1978 | Pomot et al. | 424/35 |
| 4,278,658 | 7/1981 | Hooper et al. | 424/65 |
| 4,352,794 | 10/1982 | Koch | 424/180 |
| 4,382,079 | 5/1983 | Marschner | 424/65 |
| 4,535,152 | 8/1985 | Szejtli et al. | 536/103 |
| 4,556,560 | 12/1985 | Buckingham | 424/145 |
| 4,616,008 | 10/1986 | Hirai et al. | 514/200 |
| 4,650,670 | 3/1987 | Callingham et al. | 424/65 |
| 4,659,564 | 4/1987 | Cox et al. | 424/65 |
| 4,659,696 | 4/1987 | Hirai et al. | 514/15 |
| 4,678,598 | 7/1987 | Ogino et al. | 252/174.17 |
| 4,743,440 | 5/1988 | Callingham et al. | 424/46 |
| 4,746,734 | 5/1988 | Tsuchiyama et al. | 536/103 |
| 4,788,060 | 11/1988 | Endicott et al. | 424/443 |
| 4,822,602 | 4/1989 | Sabatelli | 424/65 |
| 4,904,524 | 2/1990 | Yoh | 428/311.3 |
| 5,010,109 | 4/1991 | Inoi | 514/714 |
| 5,152,983 | 10/1992 | Nambudiry et al. | 424/60 |
| 5,306,487 | 4/1994 | Karapasha et al. | 424/76.6 |
| 5,429,628 | 7/1995 | Trinh et al. | 604/359 |
| 5,486,355 | 1/1996 | Berschied, Jr. | 424/65 |
| 5,508,028 | 4/1996 | Berschied, Jr. | 424/65 |
| 5,512,199 | 4/1996 | Khan et al. | 252/106 |
| 5,514,367 | 5/1996 | Lentini et al. | 424/59 |
| 5,518,727 | 5/1996 | Lajoie et al. | 424/400 |
| 5,525,331 | 6/1996 | Betts | 424/65 |
| 5,534,165 | 7/1996 | Pilosof et al. | 252/8.91 |
| 5,540,853 | 7/1996 | Trinh et al. | 510/101 |
| 5,543,157 | 8/1996 | Trinh et al. | 424/493 |
| 5,552,378 | 9/1996 | Trinh et al. | 512/3 |
| 5,580,851 | 12/1996 | Trinh et al. | 512/4 |
| 5,635,165 | 6/1997 | Panitch | 424/65 |
| 5,947,299 | 10/1997 | Trinh et al. . | |
| 8,946,770 | 10/1997 | Trinh et al. . | |
| 8,947,076 | 10/1997 | Trinh et al. . | |
| 8,951,184 | 10/1997 | Lucas et al. . | |
| 8,951,185 | 10/1997 | Dodd et al. . | |

5,879,666

METHODS AND COMPOSITIONS FOR REDUCING BODY ODOR

CROSS REFERENCE TO RELATED APPLICATION

This is a continuation-in-part of application Ser. No. 08/736,471, filed on Oct. 24, 1996, now abandoned.

BACKGROUND OF THE INVENTION

The human skin is naturally populated with numerous micro-organisms. These organisms are nourished by various skin secreted substances, skin cell debris, breakdown products of the skin and the organisms themselves. The "skin secretions" are eccrine and apocrine sweat, and lipid-soluble sebum. Eccrine sweat is normally odorless and remains odorless after secretion, although odoriferous food and drug substances may be excreted with it. Apocrine glands are normally associated with hair follicles and are confined mainly to the groin, perianal, areola and armpits. They produce a scanty, milky substance that is odorless upon secretion, but becomes odoriferous upon bacterial decomposition. Apocrine glands are considered to be a primary contributor for malodor.

The sebaceous glands are distributed over the skin surface except the palms and dorsae. They are most numerous on the scalp, forehead, face, back and chest. The secretion, sebum, consists mainly of fatty materials, wax esters, cholesterol and its esters and squalene. Sebum is typically associated with acne.

Specifically, body odor is most commonly caused by fatty acids on skin and from malodors from bacterial sources. The unpleasant odors are mainly organic molecules which have different structures and functional groups, such as amines, acids, alcohols, aldehydes, ketones, phenolics, polycyclics, indoles, aromatics, polyaromatics, etc. They can also be made up of sulfur-containing functional groups, such as, thiol, mercaptan, sulfide and/or disulfide groups.

Numerous attempts have been made to conceal body odors through the use of perfumes. Not only are such perfumes often inadequate at fully concealing the body odors, very often they are irritating to the user's skin. Additionally, the perfume itself may be irritating or offensive to the user's respiratory system and/or olfactory senses, as well as to nearby individuals.

Other attempts have been made to control odor through moisture absorption. Odor causing bacteria and fungi often flourish in warm, moist conditions; particularly where they have easy access to nourishment such as skin secretions and skin cell debris. Therefore, attempts are made to deprive the bacteria responsible for body odor of the moist/humid environment they need to proliferate and grow. Such efforts include the use of powders and/or antiperspirants. Powders and powder-based compositions may be difficult to apply. They may rub or even fall off onto clothing, leaving visible residue on clothing which can be quite embarrassing and inconvenient to the user. Therefore, daily use of the body powders of the prior art are undesirable and/or ineffective for day to day body odor control for the entire body. Antiperspirants are not useful in a body odor control product for use over the entire body as they may interfere with the body's thermal regulatory process by inhibiting perspiration through the action of astringent salts. Additionally, such salts may be irritating to a large number of users, particularly when applying them to sensitive areas such as the pelvic region.

Numerous other deodorant compositions aimed at combating odor associated with the skin secretions have been described in the chemical and cosmetic literature. These generally are emulsion sticks or suspensoid sticks, but also may be aerosols, roll-ons, pads, pump sprays, and even soap bars.

Known deodorants attempt to control odor through a variety of means. U.S. Pat. No. 5,525,331, to Betts, issued Jun. 11, 1996, discloses compositions which inhibit the growth of micro-organisms in the body-secretions. Deodorants may also include antibacterial compounds which help destroy and/or control the amount of bacteria present on the skin, thereby minimizing odor produced via bacterial metabolism of the skin secretions. Yet another attempt at controlling body odor is found in U.S. Pat. No. 4,382,079, to Marschner, issued May 3, 1983, which discloses the use of sodium bicarbonate as an underarm deodorant to neutralize offending body odor.

Zeolites such as those marketed under the trade name ABSCENTS by the Union Carbide Corporation and UOP are known odor absorbers. However these commonly known solid odor absorbers, in addition to known activated charcoal odor absorbers, lose functionality when wet. Therefore, when wetted by body fluids or when carried in an aqueous solution, these odor absorbers are not preferred as they loose their desired odor absorbent characteristics. Furthermore, zeolites can cause "harsh" feel if too much is deposited onto the skin.

Thus, there remains a need for an improved odor absorbing composition, which is essentially free of irritating ingredients such as perfumes or astringent antiperspirants and which is safe and effective for use on the entire body. More particularly, there is a need for a convenient, leave on composition which is capable of absorbing a broad spectrum of body odors that are not fully suppressed by the aforementioned means.

It has been discovered that such enhanced body odor control can be safely provided to the entire body by application of a composition, which is left on the skin, which incorporates odor absorbing, uncomplexed cyclodextrins into an aqueous solution. Furthermore, it has been discovered that the combination of uncomplexed cyclodextrins with low levels of antimicrobials provides a leave on skin solution with optimal body odor absorbing characteristics and extended shelf-life. It has been discovered that a particular advantage of the present invention is the ability to provide convenient, non-irritating odor protection when applied to occluded skin areas such as the pelvic region, the external vagina, the panty-line, the bra-line, and skin-folds, which may be very sensitive. Moreover, it has been discovered that the aforementioned benefits may be delivered in an aqueous solution which also optionally delivers skin aid benefits to the user such as protection and/or moisturization.

These and other objects of the present invention will become readily apparent from the detailed description which follows.

All percentages, ratios, and parts herein, in the Specification, Examples, and Claims are by weight unless otherwise stated. The term "g", as used herein, means grain. The term "ml", as used herein, means milliliter.

SUMMARY OF THE INVENTION

The present invention relates to an odor absorbing composition, which is safe for use on human skin comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, skin protectants, and mixtures thereof; an emulsifier; and an aqueous carrier. The odor absorbing compositions of the present invention may also contain an effective amount of hydrophobic antimicrobials.

The present invention also relates to methods of using the compositions of the present invention to reduce body odor and/or vaginal odor.

DETAILED DESCRIPTION OF THE INVENTION

The present invention relates to a perfume-free, odor-absorbing composition. The present invention also relates to a method of reducing body odor comprising the application of a perfume-free, odor-absorbing composition. The composition can be applied directly as a spray, poured from a bottle and applied by hand, or applied via a wipe which is wet.

The term "body fluids", as used herein, includes eccrine sweat, apocrine sweat, sebum, build up of sensible moisture from transepidermal water loss, vaginal discharge, urine, and mixtures thereof.

The term "body odor" as used herein means odors which are generated as a result of the natural functioning of a human body. Such odors include, but are not limited to odors produced by microorganisms of the human skin (i.e. bacterial decomposition of skin secretions), urine, or vaginal discharge, and mixtures thereof.

The term "entire body" means the entire external surface of human or mammalian skin.

The term "vaginal odor" relates specifically to those body odors which emanate from the pelvic region of a woman, particularly the vagina and the panty line.

A detailed description of essential and optional components of the present invention is given below.

CYCLODEXTRIN

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of about 1 % (1 gram in 100 grams of water).

Non-derivatised beta-cyclodextrin can be present at a level up to its solubility limit of about 1.85% at room temperature. When beta-cyclodextrin is applied to a wipe substrate, levels higher than its solubility limit can be used.

Preferred, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Highly water-soluble cyclodextrins are those having water solubility of at least about 10 g in 100 ml of water at room temperature, preferably at least about 20 g in 100 ml of water, more preferably at least about 25 g in 100 ml of water at room temperature. More preferred are beta cyclodextrin, hydroxypropyl alpha-cyclodextrin, hydroxypropyl beta-cyclodextrin, methylated-alpha-cyclodextrin or methylated-beta-cyclodextrin.

It is also preferable to use a mixture of cyclodextrins. Such mixtures absorb body odors more broadly by complexing with a wider range of odoriferous molecules having a wider range of molecular sizes. The levels of cyclodextrin are from about 0.1% to about 5%, preferably from about 0.2% to about 4%, more preferably from about 0.3% to about 3%, most preferably from about 0.4% to about 2%, by weight of the composition.

Concentrated compositions can also be used. When a concentrated product is used, i.e., when the level of cyclodextrin used is from about 3% to about 5%, it is preferable to dilute the composition before applying to the skin in order to avoid tacky skin feel and/or an undesirable amount of residue. Preferably the cyclodextrin is diluted with about 50% to about 2000%, more preferably with about 60% to about 1000%, most preferably with about 75% to about 500%, by weight of the composition of water.

The complexation between cyclodextrin and odorous molecules occurs rapidly in the presence of water when the solubilized cyclodextrins are first applied to the skin. Additionally, cyclodextrins which dry on the skin surfaces will once again achieve enhanced absorption capabilities when rewetted with body fluids. This is convenient for the user because the cyclodextrins, while on dry skin, will not fill their cavities with other environmental odors which would otherwise render them less efficient for absorbing body odors. More particularly, upon solubilization of the cyclodextrins by the body fluids, the isolated cavities become available to form inclusion complexes with the body odor molecules. Thus, ultimately, the availability of solubilized uncomplexed cyclodextrin is essential for an effective and efficient odor control performance. A more complete description of the cyclodextrins and cyclodextrin derivatives useful in the present invention can be found in U.S. Pat. No. 5,534,165, Pilosof et al., issued Jul. 9, 1996, which is incorporated herein by reference in its entirety.

OIL PHASE

The present invention also includes an oil phase. The oil phase is chosen from the following ingredients: skin protectants, emollients, and/or moisturizers. Saturated or hydrogenated oils are preferred. These ingredients enhance the skin feel characteristics and/or skin care benefits of the present invention. Additionally, the oil phase provides a medium in which hydrophobic antibacterials, if present, may be dissolved.

Skin protectant ingredients can prevent or reduce chafing, skin irritation and/or skin friction that may occur between skin-to-skin contact sites. Preferred skin protectants useful in the present invention include, but are not limited to: vitamin A, cod liver oil, cocoa butter, shark liver oil, dimethicone, petrolatum, white petrolatum, mineral oil, jojoba oil, and lanolin. More preferred are dimethicone, petrolatum, white petrolatum, mineral oil, jojoba oil, and lanolin. Most preferred are the dimethicones.

Moisturizers can aid in adding moisture to the skin may be included in the oil carrier of the present invention. Preferred moisturizers useful in the present invention include, but are not limited to vegetable oils and mineral oil. More preferred are hydrogenated or saturated vegetable or mineral oils. Other moisturizers useful in the present invention can be chosen from the oily moisturizers in *Cosmetic Bench Ref.* 1994, pages 46–48, incorporated herein by reference.

Emollients for softening and soothing of skin are also useful in the present invention. Emollients useful herein include tocopherol or tocopherol acetate, triglycerides, vegetable oils, or mineral oil. Other emollients useful in the present invention can be chosen from the oily emollients in *Cosmetic Bench Ref.* 1994, pages 27–31, incorporated herein by reference.

The oil phase or carrier of the present invention is present at an "effective level" which is a level which provides the desired skin benefits of the particular ingredients. Typically, the oil phase is present at a level of from about 0.1% to about 26%, preferably from about 0.2% to about 6%, by weight of the composition.

EMULSIFIER

An emulsifier must be used in the present invention. Emulsifiers are known in the art of forming oil-in-water emulsions. Preferably, a pair of emulsifiers are used for improved stability. A preferred emulsifier is a no-foaming or low-foaming emulsifier. Suitable emulsifiers are nonionic surfactants, anionic surfactants, cationic surfactants, amphoteric surfactants, zwitterionic surfactants, detersive surfactants and mixtures thereof. When an emulsifier containing one, or more, aliphatic alkyl group is used, it is preferred that it contain relatively short alkyl chains of from about 5 to about 14 carbon atoms.

Preferred nonionic surfactants are ethoxylated alkyl phenols, such as Igepal® surfactants from Rhône-Poulenc; fatty acid esters of ethoxylated sorbitans; polyethylene glycol-polypropylene glycol block copolymers, such as Pluronic®, and Pluronic R® surfactants from BASF; Tetronic® and Tetronic R® surfactants from BASF, ethoxylated branched aliphatic diols such as Surfynol® surfactants from Air Products; ethoxylated aliphatic alcohols and carboxylic acids; polyethylene glycol diesters of fatty acids; and mixtures thereof.

Preferred anionic surfactants are dialkyl sulfosuccinate, alkylarylsulfonate, fatty alcohol sulfate, paraffin sulfonate, alkyl sarcosinate, alkyl isethionate salts having suitable cations, e.g., sodium, potassium, alkanol ammonium, etc., and mixtures thereof. Preferred amphoteric surfactants are the betaines.

Also preferred are emulsifiers that have the hydrophilic groups situated between hydrophobic chains, such as Pluronic R® surfactant, Surfynol surfactants, polyethylene glycol diesters of fatty acids, fatty acid esters of ethoxylated sorbitans, dialkyl sulfosuccinate, di($C_8$–$C_{12}$ alkyl)di(C1–C2 alkyl)ammonium halides, and mixtures thereof; or emulsifiers which have the hydrophobic chains situated between hydrophilic groups, such as Pluronic surfactants; and mixtures thereof. Mixtures of these emulsifiers are also preferred.

The emulsifier is used in the present compositions at a level of from about 0.05% to about 1%, more preferably from about 0.1% to about 1% by weight of the composition. If a hydrophobic antimicrobial agent is included, more emulsifier should be included, typically from about 0.75% to about 1%, by weight of the composition.

Emulsion concentrates may also be used. Emulsion concentrates are preformed emulsions comprising an emulsifier and an oil phase and an aqueous phase. An example of an emulsion concentrate useful in the present invention is Dow Corning® 365, 35% Dimethicone Emulsion.

HYDROPHOBIC ANTIBACTERIAL AGENTS

Optionally, the present invention may include hydrophobic antibacterial compounds to help destroy and/or control the amount of bacteria present on the skin, which aids in body odor control.

Hydrophobic antibacterials useful in the present invention include triclosan, triclocarbon, eucalyptol, menthol, methylsalicylate, thymol, and mixtures thereof. Preferred are triclosan and triclocarbon.

When included in the composition of the present invention, the hydrophobic antibacterials may be at a level of from about 0.1% to about 1.5% and preferably from about 0.1% to about 0.3%, by weight of the composition.

AQUEOUS CARRIER

The cyclodextrins useful in the present invention should be solubilized in and dispersed in an aqueous carrier. The dilute aqueous solution provides the maximum separation of cyclodextrin molecules on the skin and maximizes the chance that an odor molecule will interact with a cyclodextrin molecule. An aqueous carrier is also beneficial in that it provides a clean, convenient means for applying the cyclodextrin to the desired skin sites. Additionally, an aqueous carrier may impart a degree of cleaning power in and of itself via washing away skin cell debris and skin secretions which bacteria feed upon, as well as the bacteria themselves.

The term "aqueous carrier", as used herein, means water and/or any water soluble materials suitable for use as solvents. Any water may be used, such as distilled, deionized, or tap water. Water not only serves as the liquid carrier for the cyclodextrins, but it also facilitates the complexation reaction between the cyclodextrin molecules and any malodorous molecules that are on the skin site when the composition is applied.

The aqueous carrier of the present invention will typically comprise from about 80% to about 98% of the present invention's composition. Preferably the composition of the present invention comprises the aqueous carrier at from about 85% to about 95%, by weight of the composition.

ANTIMICROBIAL PRESERVATIVE

The compositions may optionally but preferably contain solubilized, mild, water-soluble, antimicrobial preservatives which are effective for inhibiting and/or regulating microbial growth in the composition. Contamination of the compositions of the present invention by microorganisms and subsequent microbial growth can result in unsightly or malodorous compositions. Similarly, microorganisms are typically found in cyclodextrin supplies and their growth in aqueous solutions is possible. The inclusion of the antimicrobial preservatives aids in increasing storage stability of the composition of the present invention. In the present invention, the water-soluble antimicrobial preservative is included at an effective amount. The phrase "effective amount" of water-soluble antimicrobial preservative as used herein means a level sufficient to prevent spoilage, or prevent growth of microorganisms inadvertently added to the composition, for a specific period of time.

Antimicrobial preservatives useful in the present invention include biocidal and biostatic compounds (substances that kill microorganisms and/or regulate the growth of microorganisms). Suitable antimicrobial preservatives have a solubility of 0.3% or greater. In addition, suitable preservatives are those which can come into contact with skin without high irritation potential. Preferred antimicrobial preservatives are those that are water-soluble and are effective at low levels because the water insoluble organic preservatives can form inclusion complexes with the cyclodextrin molecules and compete with the malodorous molecules for the cyclodextrin cavities, thus rendering the cyclodextrins ineffective as odor controlling actives. Preservatives suitable for use in the present compositions are fully described in *The Theory and Practice of Industrial Pharmacy*, by Lachman, Lieberman, Kanig, 3rd. Edition, pages 466–467 and 520–522 (1986), and U.S. Pat. No. 5,534,165, to Pilosof et al., issued Jul. 9, 1996, both of which are incorporated herein by reference.

It is preferable to use a broad spectrum preservative such as one that is effective both on bacteria (both gram positive and gram negative) and fungi. A limited spectrum preservative such as one that is only effective on a single group of microorganisms, for example fungi, can be used in combination with a broad spectrum preservative or other limited spectrum preservatives with complimentary and/or supplementary activity. A mixture of broad spectrum preservatives can also be used.

Preferred water-soluble preservatives include the following: sodium hydroxy methylglycinate (i.e., Suttocide® A. from Sutton Labs, Chatham, N.J.); sodium benzoate; cyclic organic nitrogen compounds including imidazolidinedione compounds (such as dimethyloldimethylhydantoin i.e., Glydant® Plus from Lonza, diazolidinyl urea and imidazolidinyl urea) and polymethoxy bicyclic oxazolidine; phenyl and phenoxy compounds including benzyl alcohol, 2-phenoxyethanol and hexamidine isethionate; quaternary ammonium compounds including polyhexamethylene biguanide; low molecular weight aldehydes including formaldehyde and glutaraldehyde; halogenated compounds including chlorhexidine, chlorobutanol, and dibromopropamidine; and mixtures thereof.

In order to reserve most of the cyclodextrins for odor control, the minimal amount of effective preservative should be used. Preferred levels of preservative are from about 0.0001% to about 2%, more preferably from about 0.0002% to about 1%, most preferably from about 0.01% to about 0.5%, by weight of the composition. pH Aqueous compositions of the present invention should have a pH of from about 3 to about 10, preferably from about 3.5 to about 8, more preferably from about 3.5 to about 6. Some conventional buffering agents are known in the prior art which may be used to adjust the pH to the desired level if necessary. For example, combinations of salts and acids, such as the following examples: sodium lactate, sodium citrate, potassium phosphate, lactic acid, citric acid, phosphoric acid are useful. Some of the effectiveness of these ingredients may be lost as they complex with the cyclodextrin, so care is taking in formulating to adjust for that. Other optional buffers appear in *The Theory and Practice of Industrial Pharmacy*, Lachman, Lieberman and Kanig, Third Edition, incorporated herein by reference.

LOW-MOLECULAR WEIGHT POLYOLS

The present composition may also optionally comprises low molecular weight polyols. The phrase "low molecular weight polyols", as used herein, refers to linear organic compounds with more than one alcohol functional group per molecule wherein the molecular weight is less than about 95. Low molecular weight polyols with relatively high boiling points, as compared to water, such as propylene glycol and glycerol are preferred ingredients for improving odor control performance of the composition of the present invention. Not to be bound by theory, it is believed that the incorporation of a small amount of low molecular weight glycols into the composition of the present invention enhances the formation of the cyclodextrin inclusion complexes as the skin dries.

It is believed that the polyols' ability to remain on the skin for a longer period of time than water, as the skin dries allows it to form ternary complexes with the cyclodextrin and some malodorous molecules. The addition of the glycols is believed to fill up void space in the cyclodextrin cavity that is unable to be filled by some malodor molecules of relatively smaller sizes. Preferably the glycol used is propylene glycol. Cyclodextrins prepared by processes that result in a level of such polyols are highly desirable, since they can be used without removal of the polyols.

Optimally, the low molecular weight polyols will be added at a level effective to assist in complex formation without significantly reducing available cyclodextrin capacity to absorb the malodor molecules having larger sizes. Typically, low molecular weight polyols are added to the composition of the present invention at a level of from about 0.01% to about 1%, by weight of the composition, preferably from about 0.02% to about 0.5%, more preferably from about 0.03% to about 0.3%, by weight of the composition.

OPTIONAL INGREDIENTS

The composition of the present invention can optionally contain adjunct odor-controlling materials, such as zinc salts, water-soluble cationic polymers, water-soluble anionic polymers, water-soluble carbonate salts, water-soluble bicarbonate salts, zeolites, and activated carbon; chelating agents; colorants; and/or antiperspirants.

Optionally, but highly preferred, the present invention can include zinc salts for added odor absorption and/or antimicrobial benefit for the cyclodextrin solution. Zinc compounds have been used most often for their ability to ameliorate malodor, e.g., in mouth wash products, as disclosed in U.S. Pat. No. 4,325,939, issued Apr. 20, 1982 and U.S. Pat. No. 4,469,674, issued Sep. 4, 1983, to N. B. Shah, et al., both of which are incorporated herein by reference in their entireties. Highly-ionized and water soluble zinc salts, such as zinc chloride, provide the best source of zinc ions. The zinc salt, zinc phenolsulfonate, is preferred for use in the skin composition of the present invention; although others may also fall within the scope of the present invention. However, care must be taken in selecting zinc salts, as well as their levels, since some may be irritants to the skin and therefore are not preferred for use in the present invention.

These zinc salts aid in absorbing low molecular weight amine and sulfur-containing compounds. Low molecular weight amines and/or low molecular weight sulfur-containing materials such as sulfide and mercaptans; are components of many types of malodors such as food odors (garlic, onion), breath odor, urine odors, and particularly body/perspiration odor.

When zinc salts are added to the composition of the present invention they are typically present at a level of from about 0.1% to about 10%, preferably from about 0.2% to about 8%, more preferably from about 0.3% to about 5%, by weight of the composition.

Some water-soluble polymers such as water-soluble cationic polymer and water-soluble anionic polymers can be used in the composition of the present invention to provide additional odor control benefits. Water-soluble cationic polymers such as those containing amino functionalities, amido functionalities, and mixtures thereof, are useful in the present invention to control certain acid-type odors. Water-soluble anionic polymers such as polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990, to N. Kobayashi and A. Kawazoe, incorporated herein by reference, in its entirety. Another example of water-soluble polymers containing both cationic and anionic functionalities is a copolymer of dimethyldiallyl ammonium chloride and acrylic acid, commercially available under the trade name Merquat 280® from Calgon.

While the aforementioned water soluble polymers are useful in the present invention, when using these materials, care must be taken to insure no residual acrylic acid is present due to safety concerns associated with the presence of acrylic acid.

Water-soluble alkali metal carbonate and/or bicarbonate salts, such as sodium bicarbonate, potassium bicarbonate, potassium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention, it is preferred that incompatible metal salts not be present in the invention. Preferably, when these salts ar used, the composition should be essentially free of zinc and other incompatible metal ions, e.g., Ca, Fe, etc. which form water-insoluble salts.

Amine acid chelating agents such as ethylenediaminetetraacetic acid (EDTA) can optionally be added to the composition of the present invention in order to enhance the activity of the water-soluble, antimicrobial preservative. When a chelating agent is added to the composition of the present invention, it is typically present at a level of from about 0.01% to about 0.3%, preferably from about 0.05% to about 0.2% by weight of the composition. It is important that the composition of the present invention be essentially free of any added metal ions that can be chelated by any chelating agent that is added to the composition of the present invention because such metal ions complex with, and deactivate, the chelating agents.

Zeolites can also be used in the present invention. A preferred class of zeolites are characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfor® CP300-63, Valfor® CP300-35, and Valfor® CP300-56, available from PQ Corporation, and the CBV100® series of zeolites from Conteka.

Zeolite materials marketed under the trade name ABSCENTS® and Smelrite®, available from The Union Carbide Corporation and UOP are also preferred. These materials are typically available as a white powder in the 3–5 micron particle size range. Such materials are preferred over the intermediate zeolites for control of sulfur-containing odors, e.g., thiols, mercaptans. Zeolites are explained more fully in U.S. Pat. No. 5,429,628, to Trinh et al., issued Jul. 4, 1995, which is incorporated herein by reference in its entirety.

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

Colorants and dyes can be optionally added to the odor absorbing compositions for visual appeal and performance impression. When colorants are used, care must be taken in the selection of choosing dyes that will not color skin. Preferred colorants for use in the present compositions are highly water-soluble dyes, e.g., acid blue 3, acid blue 104, acid green 1, acid green 25, acid yellow 3, acid yellow 73 sodium salt, D&C green No. 5, 6 & 8, D&C yellow No. 7, 8, 10 & 11, D&C violet No. 2, FD&C blue No. 1 & 2, FD&C green No. 3, FD&C yellow No. 5 & 6, and mixtures thereof.

Optionally, the present skin composition may also comprise known antiperspirants and/or other known deodorant compositions not explicitly disclosed previously. Examples of antiperspirants appropriate for aqueous solutions include aluminum-zirconium tetrachlorohydrex glycine complex, aluminum-zirconium pentachlorohydrate, aluminum sesquichlorohydrate, or aluminum chlorhydrate and mixtures thereof.

Process of Making Compositions

The compositions may be prepared by oil-in-water emulsion techniques such as are commonly known in the art. Examples of such techniques are described in *Remington's Pharmaceutical Science*, Eighteenth Edition, pp. 304–306, 1990, incorporated herein by reference. The compositions of the present invention also may be prepared by a process comprising the steps of: Making a mixture by mixing an emulsifier and an oil phase until homogenous and adding an aqueous phase with mixing until the mixture is homogenous. Making a solution by adding cyclodextrin with an aqueous phase with mixing until the cyclodextrin dissolves. Making a second mixture by mixing the solution with the mixture until the second mixture is homogenous. Where desired, the second mixture may be further diluted by adding an aqueous phase with mixing until homogenous. Where hydrophobic antimicrobials also comprise the compositions, the process of making the mixture in the first step additionally comprises adding a premix with mixing to the emulsifier and the oil phase until homogenous, wherein the premix is prepared by mixing a hydrophobic antimicrobial with an emulsifier until the premix is homogenous. The term "homogenous", as used herein, means a uniformly dispersed solution. Homogeneity is indicated by a composition which is substantially smooth, lump-free and uniform in appearance. A stable emulsion remains homogeneous over a given period which is determined by the required shelf life of the composition.

As an alternative to making the mixture by mixing an emulsifier, an oil phase, and an aqueous phase; an emulsion concentrate comprising an emulsifier, an oil phase, and a minimal amount of aqueous carrier may be used. Emulsion concentrates useful in the present invention will be from about a 3-fold to about a 20-fold concentrate. The concentrated emulsion may then be diluted by adding aqueous carrier followed by addition of the remaining ingredients as discussed above. A suitable method of forming an emulsion concentrate is described in U.S. Pat. No. 5,043,155, to Puchalski et. al, issued Aug. 27, 1991. An example of an emulsion concentrate useful in the present invention is Dow Corning® 365, 35% Dimethicone Emulsion.

Other variations of processes of making the compositions which are useful include making the mixture in one step by addition and mixing of each of the ingredients. Alternatively, less than all of the ingredients may be pre-combined for subsequent combination with other ingredients or with other pre-combined ingredients to form the composition.

Equipment suitable for forming the mixtures and emulsion may be selected from those known in the art or which become known in the art. For example, suitable apparatii include dual propeller blade mixers. A turbine mixer and an in-line homogenizer using tandem rotor-stators, such as described in the above-referenced U.S. Pat. No. 5,043,155, may also be used.

The resultant emulsion containing the ingredients in their total amounts has a preferred viscosity at room temperature (i.e., 20°–25° C.) in the range of from about 10 to about 200 centipoise more preferably from about 15 to about 150 centipoise; most preferably from about 20 to about 100 centipoise.

Since the compositions of the present invention are to be applied directly to the skin, various applicators are useful for delivering the compositions to the entire body for maximum odor control. For example, the compositions are preferably deposited on a paper product such as a wipe which later is contacted with the skin to transfer the composition to the skin.

Any wipe structures and/or methods of making the wipe structures commonly known in the art may be used in the present invention. The wipe comprises a flexible dispensing means. The term "flexible dispensing means", as used herein, includes papers, cloths, non-wovens, films, foams, sponges, rollers, pads, tissues, cotton balls, and the like. Preferred wipe substrates comprise a porous material, such as the non-woven substrates, foams, or sponges, which are capable of holding the composition within the pores of the substrates. Examples of cellulosic non-wovens particularly useful and economic in the present invention are described in U.S. Pat. No. 4,191,609, Trokhan, issued Mar. 4, 1980. Further description of useful wipes and methods of making said wipes are found in World Patent 95/17175, to Mitra et. al, publication date of Jun. 29, 1995. Both references are incorporated herein by reference in their entireties.

Techniques for combining the wipe substrates with the composition of the present invention are well known in the art. Examples of common methods of combining the composition to the wipe substrate may involve coating, immersing, dipping, or spraying, the wipe substrate with the composition of the present invention. The composition of the present invention is added to the wipe substrate at level sufficient to provide the desired odor control and/or other desired skin benefits of the present invention. A convenient method of combining the composition of the present invention with the chosen substrate is to place the substrate inside an open package which will ultimately house the finished product until use. The composition is poured onto the substrate and allowed to distribute throughout. It is preferred that the homogenous composition is poured onto each wipe individually rather than onto a stack of wipes. The package is then closed and the wipes ready for use.

The composition of the present invention can also be delivered as a liquid via a spray dispenser or a bottle. Preferred is a manually activated spray dispenser to avoid the use of aerosols which may be irritating to sensitive areas of the body. Spray dispensers useful in the present invention are described more fully in U.S. Pat. No. 5,534,165 which is incorporated herein by reference in its entirety.

Methods of Use

The present invention also encompasses a method of reducing body odor on a human comprising the application of a composition described herein onto skin.

The present invention also encompasses a method of reducing vaginal odor on a human comprising applying the compositions described herein onto a pelvic region, external vagina, and/or panty-line. However, the compositions of the present invention should not be inserted into the vagina, nor applied onto the vulva.

An "effective amount" of the compositions of the present invention, as used herein, means an amount sufficient to absorb body odor to the point that it is not discernible by the human sense of smell. While the determination of an effective amount used and the number of uses per day is ultimately left to the discretion of the user, typically an effective amount will be from about 0.05 to about 0.5 grams of odor absorbing composition per use, applied about 1 to about 15 times daily, for as many days as desired by user.

The compositions of the present invention are topically applied directly to the skin or hair. The compositions can be delivered by placing the composition into a dispensing means and applying an effective amount via spraying or rubbing the composition onto the desired skin surface; typically the entire body. Preferably the dispensing means is a wipe comprising a flexible dispensing means. Distribution of the composition of the present invention can also be achieved by using a hand.

Alternatively, the user may combine the composition of the present invention with a flexible dispensing means of his or her own choosing. To do this, the user simply chooses a flexible dispensing means such as a washcloth; pours a solution of the composition of the present invention from a bottle or other suitable container over the chosen flexible dispensing means, and applies the composition to the desired area of the body. In this manner, the user may use as much or as little of the composition of the present invention as he/she desires, depending upon their intended use and degree of odor control necessary.

The following non-limiting examples illustrate the formulations and methods of use of the present invention.

EXAMPLES I, II, and III

| Ingredients | Example I Wt. % | Example II Wt. % | Example III Wt. % |
| --- | --- | --- | --- |
| Dow Corning ® 365, 35% Dimethicone Emulsion | 11.42 | 5.71 | 2.86 |
| Propylene glycol | 1 | — | 1 |
| Citric acid | 0.03 | 0.03 | 0.03 |
| Disodium phosphate | 0.02 | 0.02 | 0.02 |
| Suttocide ® A | 0.50 | — | 0.25 |
| Glydant Plus ® | — | 0.3 | — |
| Tetrasodium EDTA | — | 0.1 | — |
| Hydroxy propyl beta cyclodextrin | 1 | 1.5 | 0.5 |
| Zinc phenolsulfonate | 1.01 | — | 1.01 |
| Sodium Benzoate | — | — | 0.1 |
| Polyoxyl 40 hydrogenated castor oil | — | 0.75 | — |
| Triclosan | — | 0.25 | — |
| Distilled Water | Balance | Balance | Balance |

Prepare Example I as follows: Prepare a premix by mixing an amount of water equal to about 11.42% of the total formula weight with the Dow dimethicone emulsion mixture. Prepare an aqueous solution by mixing an amount of water equal to about 5.71% of the total formula weight with propylene glycol, citric acid, disodium phosphate, tetrasodium EDTA and zinc phenolsulfonate until all are dissolved. Prepare a second aqueous solution by mixing an amount of water equal to about 5.71% of the total formula weight with hydroxy propyl beta cyclodextrin until dissolved. Prepare a mixture by combining the aqueous solution with the premix with mixing until homogenous. Prepare a second mixture by combining remaining water of the total formula with the mixture and mixing until homogenous. Prepare a third mixture by combining the second aqueous solution with the second mixture with mixing until homogenous. Combine Glydant Plus® with the third mixture with mixing until homogeneity is achieved and the Glydant Plus® is dissolved.

Prepare Example II as follows: Prepare a premix by mixing triclosan with polyoxyl 40 hydrogenated castor oil over low heat, such as a hot plate set on low, until the triclosan is dissolved, and then combine with Dow Corning® 365, 35% Dimethicone Emulsion with mixing until homogenous. Prepare a mixture by adding an amount of water equal to about 5.71% of the total formula weight to the premix with mixing until homogenous. Prepare an aqueous solution by adding propylene glycol, citric acid, disodium phosphate, tetrasodium EDTA and zinc phenolsulfonatean to an amount of water equal to about 5.71% of the total formula weight with mixing until all are dissolved. Prepare a second aqueous solution by adding hydroxy propyl beta cyclodextrin to an amount of water equal to about 5.71% of the total formula weight with mixing until the hydroxy propyl beta cyclodextrin is dissolved. Prepare a second mixture by mixing the aqueous solution with the mixture until homogenous, and then adding remaining water of the total formula weight with mixing until homogenous. Prepare a third mixture by adding the second aqueous solution to the second mixture with mixing until homogenous. Add Glydant Plus® to the third mixture with mixing until the Glydant Plus® is dissolved and the mixture is homogenous.

Prepare Example III as follows: Prepare a premix by mixing an amount of water equal to about 2.86% of the total formula weight with Dow Corning® 365, 35% Dimethicone Emulsion until homogenous. Prepare an aqueous solution by adding propylene glycol, citric acid, disodium phosphate, and tetrasodium EDTA to an amount of water equal to about 5.71% of the total formula weight with mixing until all are dissolved. Prepare a second aqueous solution by adding hydroxy propyl beta cycyclodextrin to an amount of water equal to about 5.71% of the total formula weight with mixing until the hydroxy propyl beta cyclodextrin is dissolved. Prepare a mixture by adding the aqueous solution to the premix, and then add in remaining water of the total formula with mixing until homogenous. Prepare a second mixture by adding the second aqueous solution to the mixture with mixing until homogenous. Add Glydant Plus® to the second mixture with mixing until homogeneous.

Preparation for Application to Skin

The solutions of the present invention, such as those formed from the examples may be loaded onto a wipe or poured into a spray device or poured directly onto the skin or flexible dispensing means of the user's choosing for convenient application to the skin.

To prepare wipes

Place dry fabric or wipe substance inside an open package which will ultimately contain the finished product. Pour the composition onto the fabric to distribute throughout. Close the package for storage until consumer use.

To prepare spray

Pour the composition into the selected spray package. Close the package for storage until consumer use.

EXAMPLE IV

A woman with stress urinary incontinence finds that the wetness associated with this condition causes vaginal odor which she wants to remove from the skin and control. After urinating, the woman wipes her external vagina with a wipe containing the composition in Example I. The cyclodextrin and zinc salts in the composition complex with odors such as polycyclic compounds and amines (respectively) which are found in urine. This woman notices less odor after using the wipes.

EXAMPLE V

A large-breasted woman finds that when she exercises, she tends to experience sweating and skin chafing under the breasts. Before and after exercising, she applies the composition from Example II via a hand-held trigger-spray bottle. She sprays the composition under her breasts and the composition provides odor protection against odorous compounds that are exuded with sweat and/or sweat decomposition. This woman notices less odor and feels more comfortable after using the spray.

EXAMPLE VI

A man has severe allergies to cosmetic deodorants and antiperspirants and avoids using such products. This results in uncontrolled and embarrassing body odor. His doctor suggests applying the mild odor absorbing composition of Example III after showering. The man applies the composition to his entire body via a spray each morning after showering, and suffers no allergic reaction. The man feels comfortable without the embarrassment of lingering, uncontrollable body odor. The man keeps a pouch of wipes at work, which also contain the composition of Example III, for convenient and discrete reapplication as needed, particularly on hot and sweaty days.

What is claimed:

1. An aqueous odor absorbing composition comprising:
   a. from about 0.1% to about 5%, by weight of the composition, of solubilized, water-soluble, uncomplexed cyclodextrin;
   b. an aqueous carrier;
   c. from about 0.1% to about 36%, by weight of the composition, of an oil phase selected from the group consisting of emollients, moisturizers, and skin protectants; and
   d. an emulsifier;
   and wherein the composition is safe for use on human skin.

2. The composition of claim 1 further comprising one or more optional components selected from the group consisting of low molecular weight polyols and water soluble antimicrobials preservatives.

3. The composition of claim 2 wherein the water soluble antimicrobial preservative is sodium hydroxymethylglycinate.

4. The composition of claim 2 wherein the cyclodextrin is selected from the group consisting of beta-cyclodextrins, derivatives of beta-cyclodextrins, alpha-cyclodextrins, derivatives of alpha-cyclodextrins, gamma-cyclodextrins, derivatives of gamma-cyclodextrins, and mixtures thereof.

5. The composition of claim 4 wherein the cyclodextrin is beta cyclodextrin, hydroxypropyl alpha-cyclodextrin, hydroxypropyl beta-cyclodextrin, methylated-alpha-cyclodextrin or methylated-beta-cyclodextrin, and mixtures thereof.

6. The composition of claim 2 further comprising one or more adjunct odor controlling materials selected from the group consisting of zinc salts, zeolites, activated carbon, water-soluble carbonates, water-soluble bicarbonates, and mixtures thereof.

7. A composition wherein the composition of claim 3 is deposited on a wipe which comprises a flexible dispensing means.

8. An aqueous odor absorbing composition, comprising:
   a. from about 0.1% to about 5%, by weight of the composition, of solubilized, water-soluble, uncomplexed cyclodextrin;
   b. an aqueous carrier;
   c. from about 0.1% to about 36%, by weight of the composition, of an oil phase selected from the group consisting of emollients, moisturizers, and skin protectants;
   d. an emulsifier; and
   e. a hydrophobic antimicrobial;

and wherein the composition is safe for use on human skin.

9. The composition according to claim 8 wherein the hydrophobic antimicrobial is selected from the group consisting of triclosan, triclocarbon, eucalyptol, menthol, methylsalicylate, and thymol; and is present at a level of from about 0.1% to about 1.5% by weight of the composition.

10. The composition of claim 8 further comprising one or more optional components selected from the group consisting of low molecular weight polyols and water soluble antimicrobials preservatives.

11. The composition of claim 10 wherein the water soluble antimicrobial preservative is sodium hydroxymethylglycinate.

12. The composition of claim 8 wherein the cyclodextrin is selected from the group consisting of beta-cyclodextrins, derivatives of beta-cyclodextrins, alpha-cyclodextrins, derivatives of alpha-cyclodextrins, gamma-cyclodextrins, derivatives of gamma-cyclodextrins, and mixtures thereof.

13. The composition of claim 8 further comprising one or more adjunct odor controlling materials selected from the group consisting of zinc salts, zeolites, activated carbon, water-soluble carbonates, water-soluble bicarbonates, and mixtures thereof.

14. A pre-formed wipe composition wherein the composition of claim 8 is deposited on a wipe which comprises a flexible dispensing means.

15. The composition of claim 11 delivered as a liquid by a spray bottle.

16. A method of reducing body odor on a human comprising the application of the composition of claim 1 onto skin.

17. A method of reducing vaginal odor on a human comprising the application of the composition of claim 1 onto a pelvic region, an external vagina, and/or a panty line.

18. A method of reducing body odor on a human comprising the application of the composition of claim 3 onto skin.

19. A method of reducing body odor on a human comprising the application of the composition of claim 8 onto skin.

20. A method of reducing vaginal odor on a human comprising the application of the composition of claim 8 onto a pelvic region, an external vagina, and/or a panty line.

21. A method of reducing vaginal odor on a human comprising the application of the composition of claim 11 onto a pelvic region, an external vagina, and/or a panty line.

22. A process for making an aqueous odor absorbing composition comprising the steps of:
   a. making a mixture by mixing an emulsifier, an oil phase, and an aqueous phase until the mixture is homogenous;
   b. making a second mixture by adding cyclodextrin to the mixture of step a with mixing until the cyclodextrin dissolves and the second mixture is homogenous.

23. A process according to claim 22 further comprising making a premix by mixing a hydrophobic antimicrobial and a second aqueous phase until the premix is homogenous; and adding the premix to the mixture in step 22(a) and mixing until the mixture is homogenous.

* * * * *